(12) United States Patent
Kim

(10) Patent No.: US 7,309,357 B2
(45) Date of Patent: Dec. 18, 2007

(54) PROSTHETIC SPINAL DISCS

(75) Inventor: Chong Chol Kim, Los Angeles, CA (US)

(73) Assignee: Infinesse, Corporation, Los Angeles, CA (US)

(*) Notice: Subject to any disclaimer, the term of this patent is extended or adjusted under 35 U.S.C. 154(b) by 0 days.

(21) Appl. No.: 11/027,728

(22) Filed: Dec. 30, 2004

(65) Prior Publication Data
US 2006/0149381 A1   Jul. 6, 2006

(51) Int. Cl.
*A61F 2/44* (2006.01)
*F16F 1/06* (2006.01)
*F16F 1/08* (2006.01)
*F16F 3/02* (2006.01)

(52) U.S. Cl. .............. 623/17.13; 623/17.16; 267/166.1; 267/168; 267/180

(58) Field of Classification Search ......... 623/17.13, 623/17.16; 267/166.1, 168, 180
See application file for complete search history.

(56) References Cited

U.S. PATENT DOCUMENTS

| | | | |
|---|---|---|---|
| 1,963,053 A * | 6/1934 | Powers ................ 5/256 |
| 4,309,777 A | 1/1982 | Patil |
| 4,759,766 A | 7/1988 | Buettner-Janz |
| 4,759,769 A | 7/1988 | Hedman |
| 5,123,926 A | 6/1992 | Pisharodi |
| 5,401,269 A | 3/1995 | Büttner-Janz |
| 5,458,642 A | 10/1995 | Beer |
| 5,514,184 A | 5/1996 | Doi |
| 5,676,702 A | 10/1997 | Ratron |
| 5,782,832 A | 7/1998 | Larsen |
| 5,824,093 A | 10/1998 | Ray |
| 5,827,328 A | 10/1998 | Buttermann |
| 5,928,284 A | 7/1999 | Mehdizadeh |
| 5,989,291 A | 11/1999 | Ralph |
| 6,045,579 A | 4/2000 | Hochshuler |
| 6,231,609 B1 | 5/2001 | Mehdizadeh |
| 6,299,367 B1 * | 10/2001 | Kawakami et al. ......... 400/634 |
| 6,342,076 B1 | 1/2002 | Lundborg |
| 6,468,310 B1 | 10/2002 | Ralph |
| 6,520,996 B1 | 2/2003 | Manasas |
| 6,527,806 B2 | 3/2003 | Ralph |

(Continued)

FOREIGN PATENT DOCUMENTS

CA        2 502 058        10/2002

(Continued)

OTHER PUBLICATIONS

T.R. Lehman, K.F. Spratt, J.E. Tozzi, et. al., "Long-Term Follow-Up of Lower Fusion Patients," Spine (1987) 12:97-104.

(Continued)

*Primary Examiner*—Thomas J Sweet
(74) *Attorney, Agent, or Firm*—SoCal IP Law Group LLP; Michael D. Harris

(57) ABSTRACT

A prosthetic spinal disc uses a stiff spring or springs for resiliency between two plates that attach to adjacent vertebrae. When the disc has multiple springs, they may be adjacent, concentric or nested. Multiple springs may be spaced around the periphery of the plates. A foil metal bellows may surround the plates to prevent material from entering or exiting the space between the plates. Alternatively, the ends of the spring(s) may be machined with spikes to engage the vertebrae directly without plates.

17 Claims, 10 Drawing Sheets

U.S. PATENT DOCUMENTS

| | | | |
|---|---|---|---|
| 6,572,653 B1 * | 6/2003 | Simonson | 623/17.13 |
| 6,582,468 B1 | 6/2003 | Gauchet | |
| 6,673,113 B2 | 1/2004 | Ralph | |
| 6,723,127 B2 | 4/2004 | Ralph | |
| 6,752,577 B2 * | 6/2004 | Chen et al. | 411/508 |
| 6,758,861 B2 | 7/2004 | Ralph | |
| 6,964,686 B2 * | 11/2005 | Gordon | 623/17.14 |
| 2001/0051829 A1 | 12/2001 | Middleton | |
| 2003/0078667 A1 | 4/2003 | Manasas | |
| 2004/0024463 A1 * | 2/2004 | Thomas et al. | 623/17.16 |
| 2004/0102849 A1 | 5/2004 | Ralph | |
| 2004/0204763 A1 | 10/2004 | Ralph | |
| 2004/0225361 A1 * | 11/2004 | Glenn et al. | 623/17.12 |
| 2005/0027364 A1 | 2/2005 | Kim | |
| 2005/0043796 A1 | 2/2005 | Grant | |
| 2005/0113924 A1 | 5/2005 | Buttermann | |
| 2005/0197702 A1 | 9/2005 | Coppes | |
| 2005/0228500 A1 | 10/2005 | Kim | |
| 2005/0251260 A1 | 11/2005 | Gerber | |
| 2006/0052872 A1 | 3/2006 | Studer | |
| 2006/0064169 A1 | 3/2006 | Ferree | |
| 2006/0069436 A1 | 3/2006 | Sutton | |

OTHER PUBLICATIONS

V. Traynelis and R. Haid, "Spinal Disc Replacement: The Development of Artificial Discs," Spine Universe (Oct. 10, 2001).

Link SB Charite disc from Waldemar Link GmbH & Company of Germany.

Bryan cervical disc from Spinal Dynamics Corporation of Seattle, Washington.

Qi-Bin Bao and Hansen A. Yuan, Artificial Disc Technology, Neurosurg. Focus, vol. 9, Oct. 2000, New York, USA.

M.F. Eijkelkamp, et al., Ch. 2 Requirements for an Artificial Intervertebral Disc, The International Journal of Artificial Organs, 2001, 24:311-321.

Craig W. Martin, Artificial Cervical and Lumbar Disc Implants: A Review of the Literature, WorkSafe Program Design Division, Apr. 13, 2005.

* cited by examiner

PROSTHETIC SPINAL DISCS

BACKGROUND OF THE INVENTION

1. Field of the Invention

The present invention relates to prosthetic devices used to replace diseased or damaged spinal discs.

2. General Background and State of the Art

The adult spine has 26 vertebrae (depending how one counts) with fibrocartilage, intervertebral discs between adjacent vertebrae. The vertebrae include seven cervical vertebrae in the neck, 12 thoracic vertebrae below the neck, five lumbar vertebrae of the lower back, one sacrum below the lumbar region and one coccyx, or tailbone. The discs form strong joints, separate, cushion and allow flexure and torsion between the vertebrae.

When functioning properly, the vertebrae and discs allow a person to bend forward, backward and to the sides and to twist. To accomplish this, the discs permit adjacent vertebrae six degrees of motion: vertical (compressing to absorb shock and tension), bending forward and backward, bending to the sides and twisting. The cervical and lumbar discs also can be thicker anteriorly to contribute to lordosis. Thoracic discs are more uniform. Unfortunately, disc disease limits spinal motion or cushioning or only permits the motion with pain.

Each intervetebral disc has a central area composed of a colloidal gel, called the nucleus pulposus, on a surrounding collagen-fiber composite structure, the annulus fibrosus. The nucleus pulposus occupies 25-40% of the disc's total cross-sectional area. The nucleus pulposus usually contains 70-90% water by weight and mechanically functions like an incompressible hydrostatic material. The annulus fibrosis surrounds the nucleus pulposus and resists torsional and bending forces applied to the disc. The annulus fibrosis thus serves as the disc's main stabilizing structure. The annulus fibrosus resists hoop stresses due to compressive loads and the bending and torsional stresses produced by a person bending and twisting. The fibers of the annulus form lamellae, individual layers of parallel collagen fibers, that attach to the superior and inferior end plates of adjacent vertebrae. Vertebral end-plates separate the disc from the vertebral bodies on either side of the disc.

The anterior longitudinal ligament, which is anterior to the vertebral bodies, and the posterior longitudinal ligament, which is posterior to the vertebral bodies and anterior to the spinal cord hold the spinal structure together. The muscles of the trunk provide additional support.

Trauma or disease may displace or damage spinal discs. A disc herniation occurs when annulus fibers weaken, and the inner tissue of the nucleus bulges out of the annulus. The herniated nucleus can compress a spinal nerve, which results in pain, loss of muscle control or even paralysis. Alternatively, disc degeneration results when the nucleus deflates. Subsequently, the height of the nucleus decreases causing the annulus to buckle in areas where the laminated plies are loosely bonded. This also causes chronic and severe back pain.

Whenever the nuclear tissue is herniated or the disc degenerates, the disc space narrows and the adjacent vertebra may lose much of their normal stability. In many cases, to alleviate pain from degenerated or herniated discs, a surgeon removes the nucleus or the disc as a whole and fuses the two adjacent vertebrae together. While this treatment usually alleviates the pain, the patient loses all disc motion in the fused segment. Ultimately, this procedure places greater stress on the discs adjacent to the fused segment as the adjacent discs compensate for lack of motion. The added stress may lead to premature degeneration of those adjacent discs. See, Lehman, T. R., Spratt, K. F., Tozzi J. E., et al., "Long-Term Follow-Up of Lower Lumbar Fusion Patients." *Spine* (1987) 12:97-104.

Surgeons have replaced damaged discs with prosthetic devices. The devices generally take four approaches, hydraulic, elastic, mechanical, and composite. Traynelis V. and Haid R. "Spinal Disc Replacement: The Development of Artificial Discs." *Spine Universe* (Oct. 10, 2001), gives an overview of the state of the art as of 2001.

A useful disc prosthesis must satisfy several criteria. It must maintain proper spacing between adjacent vertebrae, permit desired motion, provide stability and absorb shock. The disc prosthesis should not shift axial load significantly from where a natural disc would apply those loads. Any disc prosthesis should replicate normal ranges of motion from front to back, side to side, vertically and in torsion. The prosthesis also must constrain motion.

Any disc prosthesis must retain its initial functional characteristics for many years and over many cycles. Studies estimate that a typical patient with a prosthesis will need it for 50 years. Replacing a worn-out prosthesis should be avoided. The average persons takes 2 million strides annually and bends over 125,000 times per year. Thus, any prosthesis cycles more than 100 million times in 50 years.

The prosthesis materials must be biocompatible and not corrode. It also should not inflame surrounding tissue. Because of the millions of cycles to which the prosthesis material will be subjected, the material must have a high fatigue strength. It also should give off minimal debris. Some believe that the prosthesis also should show up well on X-ray images. Likewise, the prosthesis must be capable of fixation to bone. In addition, the design should protect against a catastrophic failure from the failure of any individual component. In addition, the prosthesis should guard against damage to surrounding tissues, particularly the spinal cord.

The Link SB Charité disc from Waldemar Link GmbH & Co of Germany has been widely implanted. It consists of an ultra high molecular weight polyethylene spacer between two endplates. The Charité disc provides only three degrees of freedom and no load support. It allows for flexion and extension, lateral bending and rotation but not compressive movement or lateral or sagittal shear.

The Bryan cervical disc from Spinal Dynamics Corp. of Seattle, Wash. uses an elastic nucleus between two metal plates. A flexible membrane between the plates surrounds the nucleus. The Bryan disc also provides five degrees of freedom and only partial load support. It allows for flexion and extension, rotation, lateral bending and lateral and sagittal shear. This disc is recommended only as a replacement for cervical discs.

Ray, U.S. Pat. No. 5,824,093 (1998), also is an example of the elastic type of disc prosthesis. The patent discloses a disc prosthesis having upper and lower end plates with a constraining jacket and a deformable gel core. End plates, which attach to adjacent vertebrae, apply load to the gel causing the gel to deform. Friction causes one problem in this device. The gel is encapsulated, and as it deforms, the expansion takes place laterally along the insides of the top and bottom surfaces. Over time, as the surfaces of the gel capsule and top and bottom plates change, the friction changes. This causes the prosthetic disc to function improperly.

The hydrogel disc replacement is an example of the hydraulic approach. A hydrogel implant replace only the nucleus; the annulus fibrosis is not replaced. Raymedica, Inc. of Bloomington, Minn., manufactures a PDN prosthetic disc nucleus implant that consists of a woven polyethylene jacket constraining a hydrogel core. The jacket is flexible but inelastic. Therefore, the jacket allows the hydrogel core to deform and reform as it is loaded and unloaded, but the jacket limits the core's horizontal and vertical expansion Some are concerned that prostheses that use gel or polymer will lose the resiliency or the resiliency will change over the many cycles of loading and unloading. Others are concerned that as the molecules of the resilient material move relative to each other and move with respect to the material encapsulating the gel, some molecules or groups of molecules will break off and enter surrounding tissue. The body recognizes these molecules as foreign bodies and attacks them. This biological activity can cause the prosthesis to lose its grip with the surrounding bone tissue.

Instead of a gel for resiliency, several patents propose using springs. For example, Patil, U.S. Pat. No. 4,309,777 (1982), has springs spaced around the periphery of opposing cups. However, Patil also fails to provide natural motion for adjacent vertebrae. Beer, U.S. Pat. No. 5,458,642 (1995), spaces the springs laterally. Ratron, U.S. Pat. No. 5,676,702 (1997), relies on a specially shaped resilient member. Larsen, U.S. Pat. No. 5,782,832 (1998), has a linkage between the top and bottom plates with resilient springs between those plates.

Butterman, U.S. Pat. No. 5,827,328 (1998), suggests having different springs for different embodiments of its invention. Mehdizadeh, U.S. Pat. No. 5,928,284 (1999), shows a disc prosthesis that threads between vertebrae. Springs push apart parts of the threaded member. Ralph, U.S. Pat. No. 5,989,291 (1999), uses Belleville washers for its resiliency. Finally, Pisharodi, U.S. Pat. No. 5,123,926 (1992), spring-biases the spikes used to hold the prosthesis in place. The springs also expand the prosthesis.

Each of these devices is problematical. When prior art prostheses use coil springs, adjacent coil windings can touch or rub against each other. If the coils touch and depending on how they touch, the touching can create a sound, which is unnatural and can be unpleasant. Further, when adjacent coils rub against each other, microscopic pieces of metal can rub off the spring. The body can attack these pieces and create an immune reaction, which can loosen the spring. Using a plastic spring does not solve the problem because plastic molecules also can rub off. Further, plastic may not be strong enough for the small springs necessary. Fortunately, one can manufacture small springs with the necessary spring constants with this application. Further, one can design metal springs that maintain the same spring constant over the anticipated useful life of the prosthesis.

Using springs can be advantageous. They are reliable. Springs are intrinsically stable and designed for cyclic loading. However, prior art spring prostheses fail to consider proper spring design. In particular, the diameter of the spring wire and the way in which the wire is wound affect the spring's mechanical properties. Moreover, the spring must be limited in size. The spring must have a diameter no greater than the outside dimensions of adjacent vertebrae, and the spring must cause the prosthesis to be no taller than the disc being replaced.

Prior art metal spring prosthesis usually have alignment problems. If the applied force is not aligned with the axis of the spring, the spring may cant. These problems can cause the springs to work unevenly.

The patient's height and weight and the particular disc to be replaced affect the size and properties of the spring. Thus, for example, the spring constant and disc configuration are very different for a prosthesis to replace the disc between the forth and fifth lumbar vertebra in a 6'2", 200 lb. (188 cm, 91 kg) male then for the disc between the third and fourth thoracic vertebra in a 5'2", 115 lb. (157 cm, 52 kg) female., (Metric/English conversions are approximate.) Using the correct spring or group of springs replicates the functions of a healthy disc. Having many different versions of specially configured springs available for a surgery can be costly, however. In addition, fabrication costs for specialized springs are greater.

Surgical procedures for disc replacement are very complex and subject to many complications. State of the art prostheses contribute to the complexity of disc replacement surgery. Aligning and securing present prostheses can be very difficult and time consuming.

INVENTION SUMMARY

With these potential problems of the state of the art, it is a general object of the invention to provide an intervertebral disc prosthesis and surgical method for implanting the prosthesis to avoid some problems in the prior art. Another object of the invention to provide an intervertebral prosthetic device that replicates the mechanical properties of a natural intervertebral disc.

These and other objects will be apparent to those skilled in the art.

The prosthetic spinal disc of the present invention fits between two adjacent vertebrae. It uses one or more stiff springs for resiliency between two adjacent vertebrae. The springs may be a single coil spring of a material and spring wire diameter to provide desired resiliency, or multiple springs adjacent or nested in each other may be used. The spring(s) may mount between upper and lower fittings or plates, and each plate or fitting may engage the vertebrae. Alternatively, the ends of the spring(s) may be machined to engage the vertebrae directly.

The spring allows six degrees of freedom between the upper and lower sections. Spring compression and tension permits vertical movement of the sections relative to each other as adjacent vertebrae are loaded and unloaded. The spring also allows forward, backward and side to side bending so that the person can bend over, arch his or her back, or bend to the right or left. The spring also may permit some twisting about the axis.

Coil springs are preferred. As the spring performs these tasks, the design of the spring may prevent adjacent coils from contacting each other or minimizes contact of adjacent coils. This is accomplished by having a taper in the coil spring such that the outside diameter of one coil is slightly less than the inside diameter of the adjacent coil (analogizing the helical coil to a circle). In one embodiment, the larger diameters are adjacent the upper and lower sections, and the coil tapers toward its longitudinal center (an hourglass shape). In another embodiment, the spring is conical, having a larger diameter at one end and tapering to a smaller diameter at the other end. For example, the maximum diameter $D_{max}$ may be 22 mm (0.87"), and the minimum diameter, $D_{min}$ may be 12.7 mm (0.5"). The coils may be helical, or they may form other shapes such as an ellipse.

As will be evident, length of the spring in the present invention must be relatively short because of the short space between vertebrae. Because of the loads involved, the radius of the wire that forms the spring will be relative large (e.g., 0.001 in (0.0254 mm)). Therefore, the spring constant will be quite high. Such a high spring constant by itself could prevent coil-to-coil contact under most loads.

In theory, a single spring could provide sufficient force. Applicant anticipates that the spring or springs will require an overall spring constant approaching 2,000 N/mm (11,414 lbs/in). Achieving that spring constant with a single spring coil in the dimensions of the prosthesis is difficult, especially because of the small space between the vertebrae. Therefore, having multiple springs that could be spaced around the prosthesis or interlaced likely is necessary. Moreover, a single spring may cant. Using multiple, spaced-apart springs may avoid this potential problem.

The preferred spring material is a biological metal such as titanium alloys and alloys of cobalt-chromium-molybdenum, called "cobalt-chrome." Generally, cobalt-chrome surgical wire has the properties to be used as a spring capable of providing the necessary functions of an artificial spinal disc for humans when implanted in the proposed designs. The elasticity and compressibility of the spring can change for different mechanical properties. Those changes are affected by:

The physical property of the biometal that forms the spring;
The number of coil turns and the shape and size of each coil turn;
The number of separate springs;
The dimension and the cross-sectional shape of the spring wire;
The cross-section diameter of the spring wire;
Variations in the cross-sectional geometry at different parts of the spring coil; and
The placement of various spring wire cross-sections along the coils and the transitions between different cross sections.

When loads compress the spring to its maximum compression based on the patient's weight and the compressive forces on the spring during activity, the coil turns do not rub against each other. In some instances, however, where the spring tapers toward its center (i.e., hourglass shape), non-adjacent coils may touch each other momentarily at maximum loading. Conical springs only contact the end plates when they bottom out.

The springs are designed to replicate the characteristics of natural discs. Accordingly, the springs act to cushion adjacent vertebrae gently and to allow normal, six degrees of freedom movement. The disc may also have multiple springs of similar or different configurations mounted in particular patterns to make the disc prosthesis replicate a normal disc better. Moreover, using multiple springs can facilitate increased loading and damping functions, counteract natural reactive twist associated with a single spring, and provide optimum six degrees of motion support.

Designing the spring so that the spring constant varies over distance may also help replicate natural disc function. Under normal loads, spring displacement would vary at one rate, but as the load increased, the rate of change of spring displacement as a function of load would decrease. Spring configuration and variances in the spring wire shape and diameter along the spring would have the principal affects on the load curve.

In one embodiment, springs mount between and are preferably welded to upper and lower plates. The plates may be flat or slightly curved. Welding the spring to the plates also prevents or minimizes ledges or crevices when the spring contacts the plates. Ideally, the welding material is shaped to provide a smooth transition between the spring material and the plate. Welding material also can fill the space between the edge of the plate and the outside of the spring to prevent the formation of a ledge. Applicants recognize that welding techniques are used more easily on the outside of the spring than on the inside of the coils, which is difficult to reach.

Instead of direct welding, the plates may have grooves or open slots to receive the beginning and end of the coil. The spring also may be welded in such grooves or slots.

If the prosthesis does not have plates, the spring coils should be designed such that their contact with the vertebrae does not create unacceptable localized stress on the vertebrae. Increasing the contact area of the spring to the vertebrae by shaping the coil wire and shaping the coil itself will minimize localized stress. Flattening the outer, top surface of a round diameter wire coil increases the contact area while flattening the bottom surface reduces the overall compressed spring thickness. Likewise, having a low spring pitch at the ends of the spring increases the length of the spring that contacts the vertebrae.

If the coil wire is flattened using a metal forming process such as grinding or machining, spikes can be formed on the flat surface that contacts the vertebrae. The coil wire also can be flattened by forging in designated portions. Spikes, which engage the vertebrae and secure the spring in place, can be grinded, machined or formed by electric discharge on the unflattened regions.

The present invention may have a circumferential skirt between the top and bottom plates. Such a skirt would prevent tissue from contacting the springs or the region between the plates. The present invention preferably uses a skirt of cobalt-chrome foil in a bellows configuration. The skirt preferably is welded to the periphery of the top and bottom plates.

BRIEF DESCRIPTION OF THE DRAWINGS

FIG. 5 shows the disc under normal load, and FIG. 6 shows the disc compressed under a heavier load.

FIG. 11 shows the disc under normal load, and FIG. 12 shows the disc compressed under a heavier load.

DETAILED DESCRIPTIONS OF EXEMPLARY EMBODIMENTS

Figure 1:
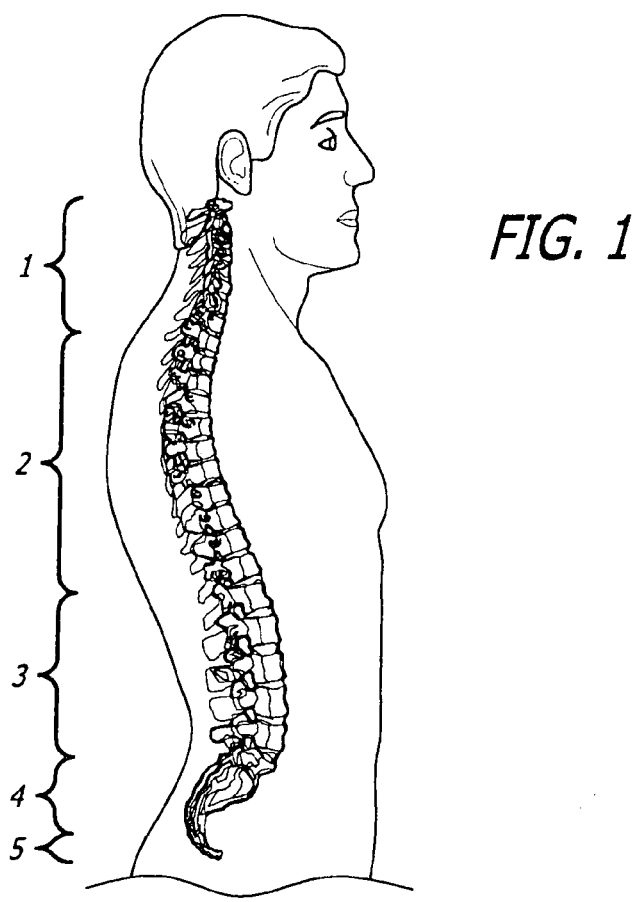
FIG. 1 is a background drawing showing a side view of the human spine.

FIG. 1 is a representation of a human spine. The vertebrae include seven cervical vertebrae 1 in the neck, 12 thoracic vertebrae 2 below the neck, five lumbar vertebrae 3 of the lower back, one sacrum 4 below the lumbar region and one coccyx 5.

Figure 2:
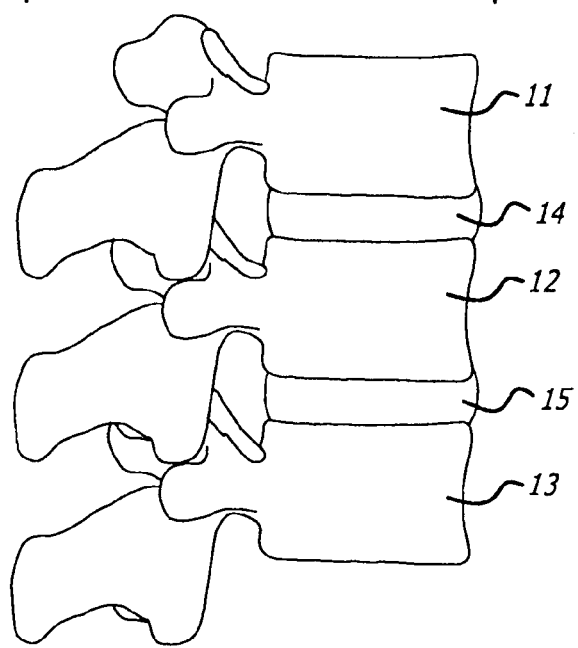
FIG. 2 is a background drawing showing a side view of three adjacent vertebrae.
Figure 3:
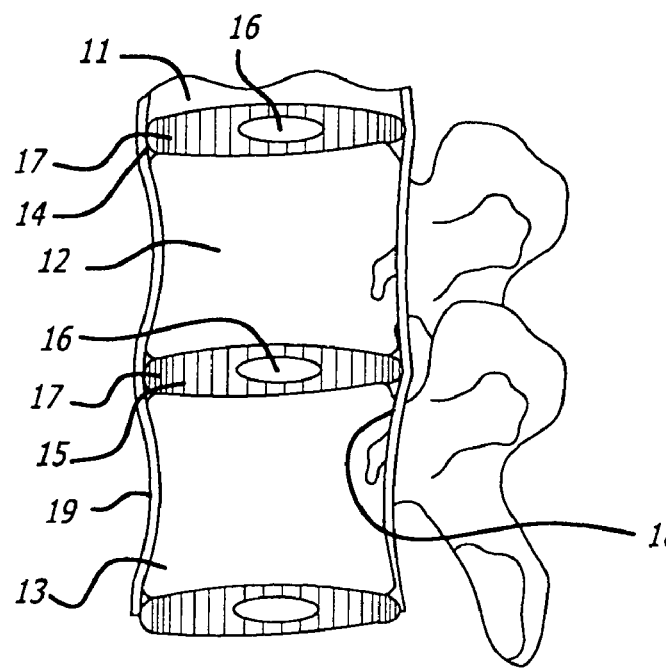
FIG. 3 is a side sectional view of portions of two adjacent vertebrae that shows the intervertebral disc between the vertebrae.

The adjacent vertebral bodies 11, 12 and 13 (FIGS. 2 and 3) are separated by intravertebral discs 14 and 15. Each disc has a nucleus pulposus 16 surrounded by an annulus fibrosus 17. See also FIG. 4. FIG. 3 also shows the posterior longitudinal ligament 18 and the anterior longitudinal ligament 19, which secure the vertebrae and disc together. Other ligaments, which are not discussed, also are present.

Figure 4:
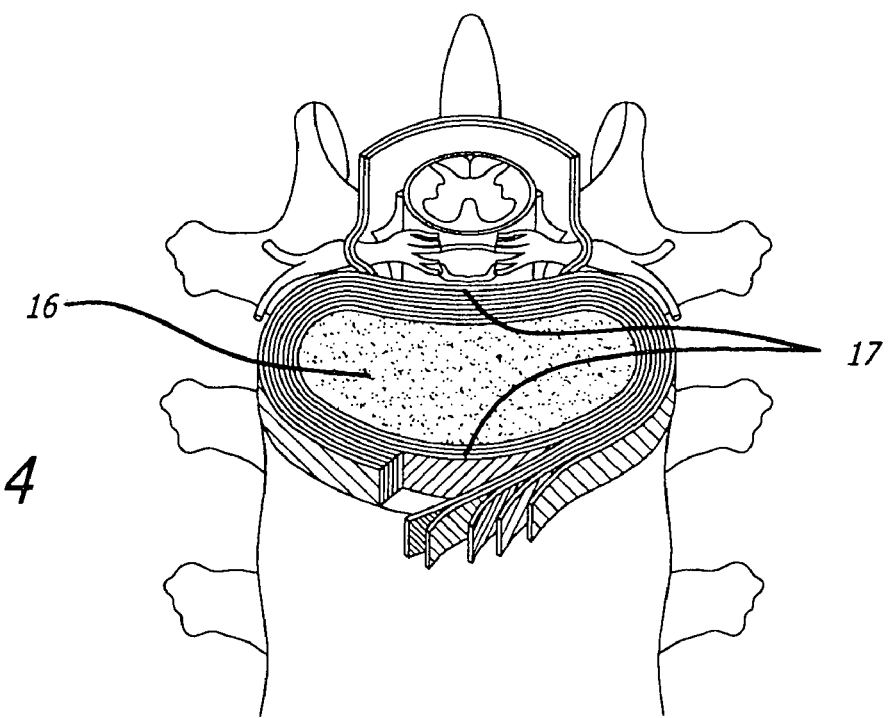
FIG. 4 is a background, perspective drawing showing a representation of the intervertebral disc.
Figure 5:
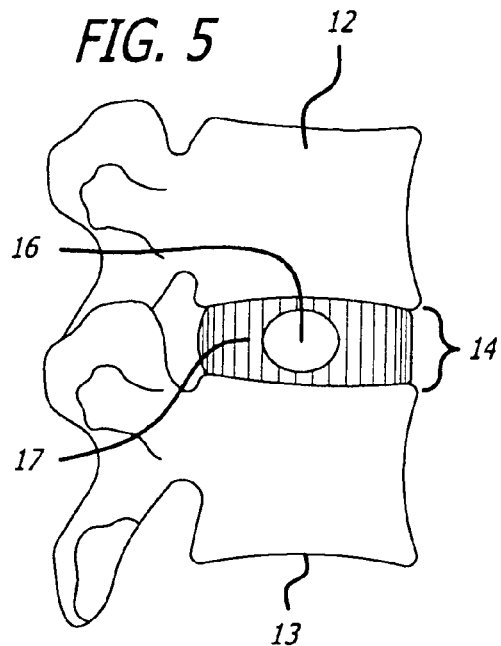
FIGS. 5 and 6 are side sectional views two adjacent vertebrae with an intervertebral disc between the vertebrae.
Figure 6:
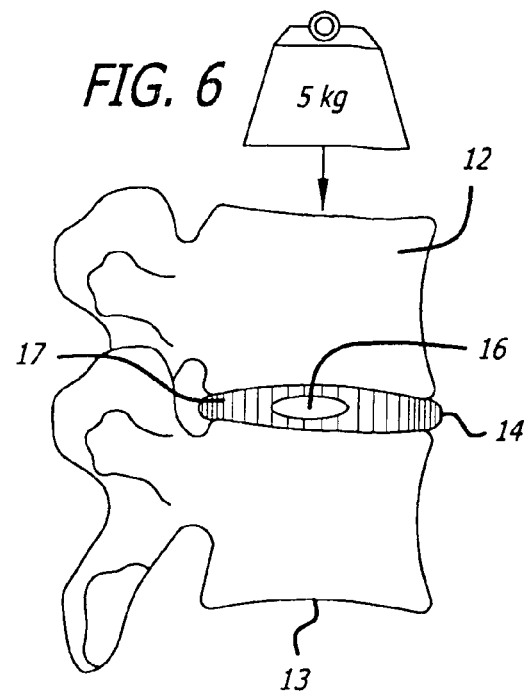

The representation of a disc in FIG. 4 shows the nucleus pulposus surrounded by the outer annulus fibrosus. The annulus fibrosus acts as a constraining ring primarily composed of collagen. It allows the intervertebral disc to rotate or bend without significantly affecting the hydrostatic pressure of the nucleus pulposus. The nucleus pulposus consists of proteoglycan, which has an affinity for water molecules. The water hydrates the nucleus pulposus. The hydrated nucleus generates hydraulic effects to act as a shock absorber for the spine. FIGS. 5 and 6 show that effect. A heavy load applied to adjacent vertebrae 12 and 13 compresses disc 14. The nucleus pulposus becomes loaded. It is only slightly compressible, however. Therefore, the force is transmitted to the annulus fibrosus which are tensioned. The bands of the annulus fibrosus stretch to absorb the force and then contract to their original length.

The pattern that FIGS. 1 through 6 shows continues to the adjacent vertebrae. Each vertebra is different from its adjacent vertebra, however. For example, lumbar vertebrae are larger than thoracic ones. See FIG. 1. In addition, cervical and lumbar discs are thicker anteriorly, which contributes to lumbar lordosis. Discs for the thoracic vertebrae are more uniform.

Figure 7:
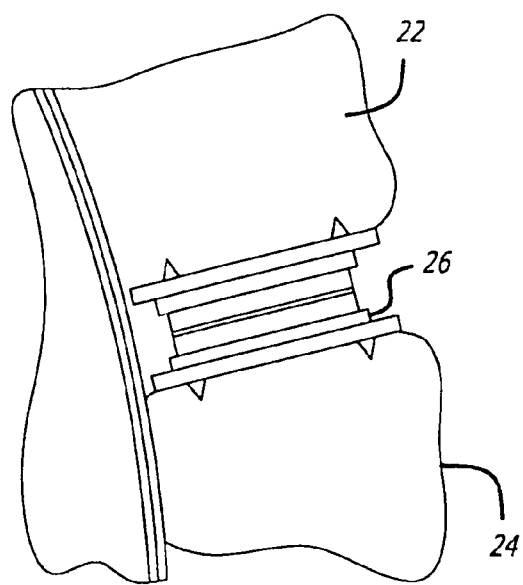
FIG. 7 shows a portion of a human spine with a prior art disc prosthesis between two adjacent vertebrae.
Figure 8:
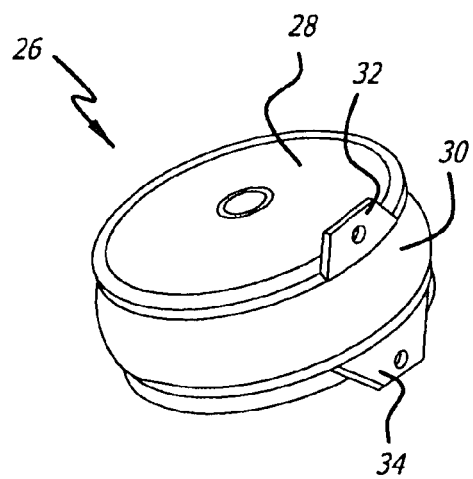
FIG. 8 is a perspective view of another prior art disc prosthesis.

The prior art recognizes that natural intervertebral discs can be replaced with a disc prosthesis. Thus, FIG. 7 shows two adjacent vertebrae 22 and 24 with disc prosthesis 26 replacing the natural disc. Disc prosthesis 26 is a representation of the Charité prosthesis. FIG. 8 shows the previously mentioned Bryan cervical disc 26. Note that it is only recommended as a prosthesis for the cervical vertebrae. It has an elastic nucleus (not visible) between two metal plates 28 (only one shown). A flexible membrane 30 between the plates surrounds the nucleus. Applicant understands that current models of the Bryan cervical disc do not have the small tabs 32 and 34.

The present invention replaces natural intevertabral discs with a system that uses one or more springs to provide spinal resiliency. The spring material is preferably titanium or cobalt-chromium-molybdenum. These materials are the most common metals used inside the body because of their strength and resistance to wear, corrosion and biological activity. Though other materials could be used (e.g., plastics), they likely lack the proper mechanical, chemical and biological particles for the environment of this invention.

The spring or springs that the present invention uses have two primary configurations although other shapes are possible. One principal configuration for the spring is shown in FIG. 17. There, spring 70 is a coil spring in which the spring diameter at its longitudinal center 72 is less than the spring diameter at the longitudinal ends 74 and 76. On the other hand, spring 78 (FIG. 16) has a larger coil diameter on one end 80 and a smaller coil diameter at the other end 82.

Though a spring with a constant coil diameter is acceptable, the spring in these exemplary embodiments provides greater permissible compression without having adjacent coils contact each other. Minimizing coil contact is valuable. Even slight contact creates friction and sound that detract from performance. In addition, when coils contact each other, microscopic amounts of metal may break off from the spring. As these microscopic metal particles migrate away from the spring, they might create biological reactions that may weaken adjacent tissue such as the vertebrae.

Some contact between adjacent coils may be inevitable, especially under extraordinary loads as when landing after jumping from a high platform, but minimizing contact still is desirable. If spring contact occurs rarely such and only under the most extreme conditions, the adverse consequences would be minor. Thus, depending on the spring constant, some adjacent coils may come into contact when the spring is fully compressed.

Depending on the spring pitch and the spring wire diameter, a spring that does not taper could be designed to resist having adjacent coils touch within maximum load. Such a spring likely would have to be taller, however. That may be impractical for the tight spaces of the prostheses of the present invention.

Note also that spring 70 (FIG. 17) has five turns, but spring 78 (FIG. 16) only has three turns. The choice of the number of turns depends on many factors including the spring wire diameter and material, the anticipated load, the available space between the vertebrae, the number of springs used in the prosthesis, and other factors. The spring, therefore, may have less than one turn, or it may have multiple turns. The present invention will use the spring winding that yields preferred results.

Figure 16:
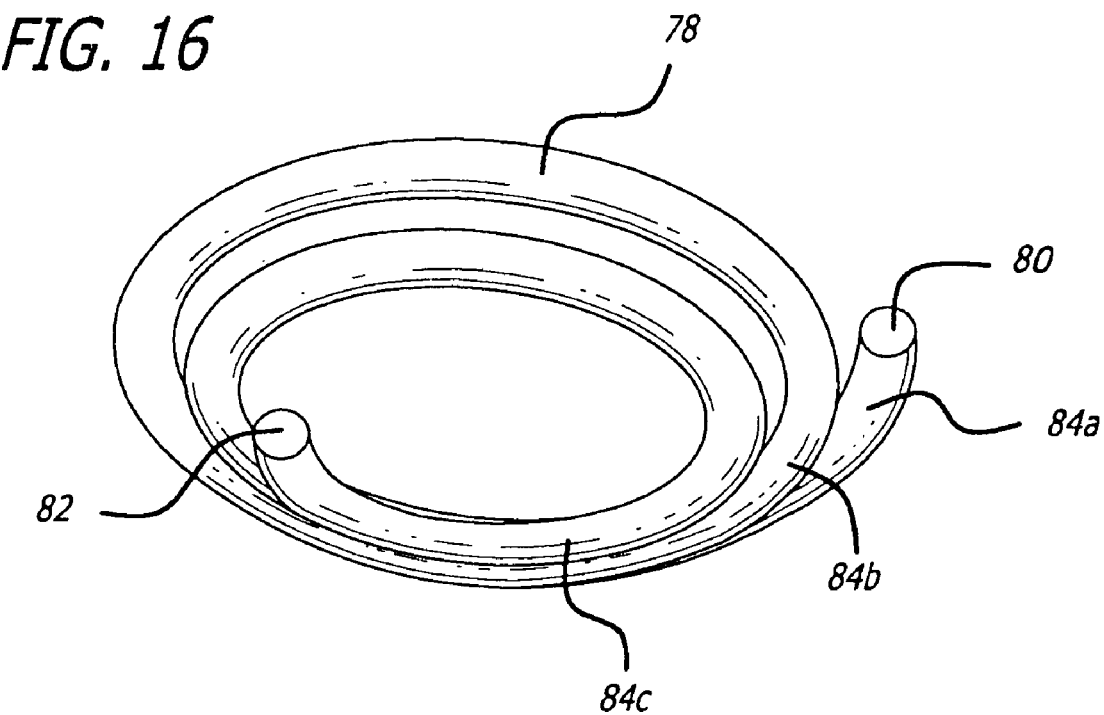
FIG. 16 is a perspective view of a spring for the present invention.
Figure 17:
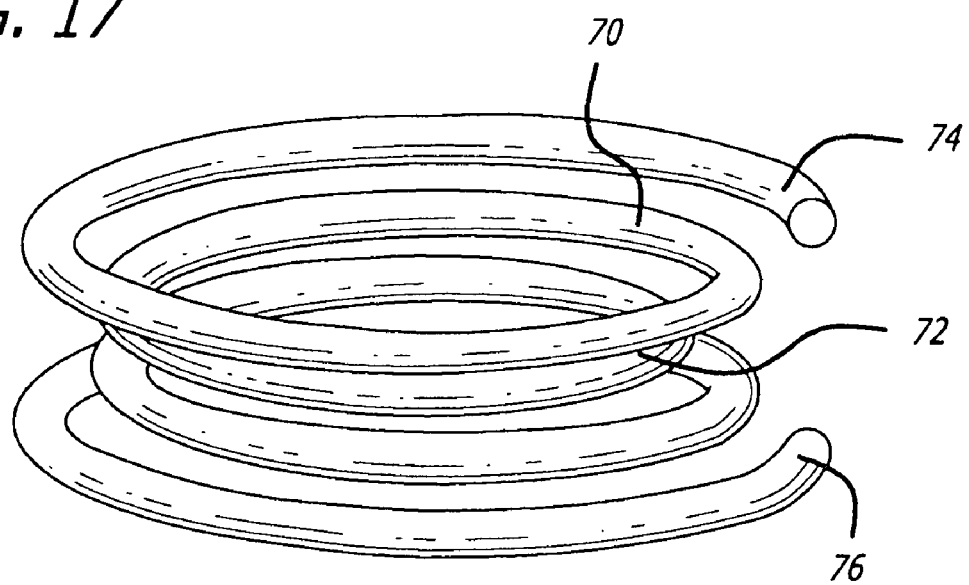
FIG. 17 is a perspective view of another spring for the present invention.

In FIGS. 16 and 17 (and other figures), the wire that forms the coil has a circular cross-section. That is often preferable, especially for fabrication. The present invention also can use spring wire that has noncircular cross-sections over its entire length or over a portion of the wire. For example, the spring could have a section or the entire length that elliptical with a major axis parallel or perpendicular to the longitudinal axis of the spring. The dimensions also may vary along the spring wire. Thus, the ratio of the major axis to the minor axis may change. Similarly, the major axis may be parallel to the longitudinal axis of the spring over part of the spring and perpendicular or at an angle at other parts. Likewise, even with a circular spring wire, the wire diameter may vary over the length of the spring.

Insofar as different sections have different cross-sections, the spring wire would provide smooth transitions between the various cross-sectional shapes. Testing will determine if noncircular cross-sections are advantageous, and if so, what they should be.

After immobilizing the adjacent vertebrae above and below the damaged or diseased natural disc, the surgeon installing the prosthetic spinal disc of the present invention first removes the natural disc. He or she cuts flat facing surfaces in the adjacent vertebrae. Alternatively, the surface may be concave. More complex surfaces are possible, but applicant believes that flat or concave surfaces are easier to form.

The prosthesis has a vertical dimension to fit within the space between the adjacent vertebrae. The vertical dimension of the fitting should be the same as the vertical dimension of the natural disc. That makes the mechanics of the prosthetic disc the same as the natural disc. Because disease or injury may make the natural disc shorter, the prosthetic disc may have the same height as the pre-diseased or pre-injured natural disc.

The fitting has at least one internal cavity. Fitting 88 of the exemplary embodiment of FIG. 9 has a single cavity bounded by the top and bottom parallel plates 90 and 92. Alternatively, the region between the plates could be divided into separate regions with internally-facing projections from the top and bottom plates creating the cavities. The exemplary embodiment shows a single cavity, however.

The fitting 88 has an upper section and a lower section movable relative to each other. In one exemplary embodiment (FIGS. 9, 10 and 13), the upper and lower sections of fitting 88 are flat, parallel plates 90 and 92. The present invention has at least one spring received within the cavity to bias the upper and lower plates apart. Six internal coil springs 94, 96, 98, 100, 102 and 104 are between the flat plates in the exemplary embodiment of FIG. 9. Pairs of opposite-wound spring coils are arranged to cancel the compressive torque reaction associated with a given coil. A single spring disc would need an oppositely wound concentric or nested spring to cancel the twist movement that occurs when a single spring compresses.

Figure 9:
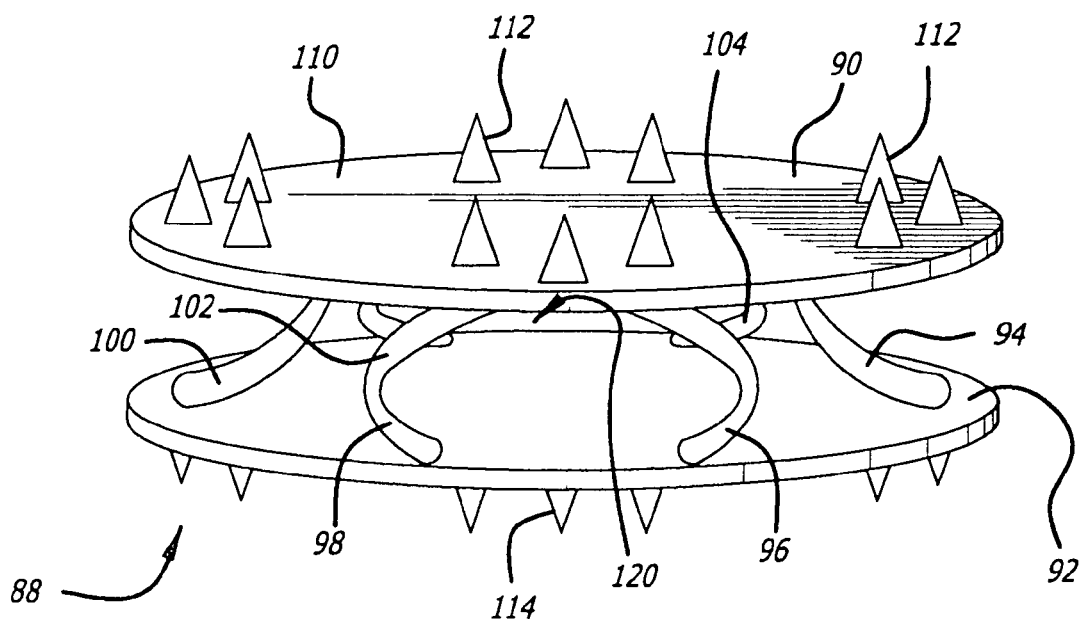
FIG. 9 is a perspective view of one embodiment of the prosthetic spinal disc of the present invention.
Figure 10:
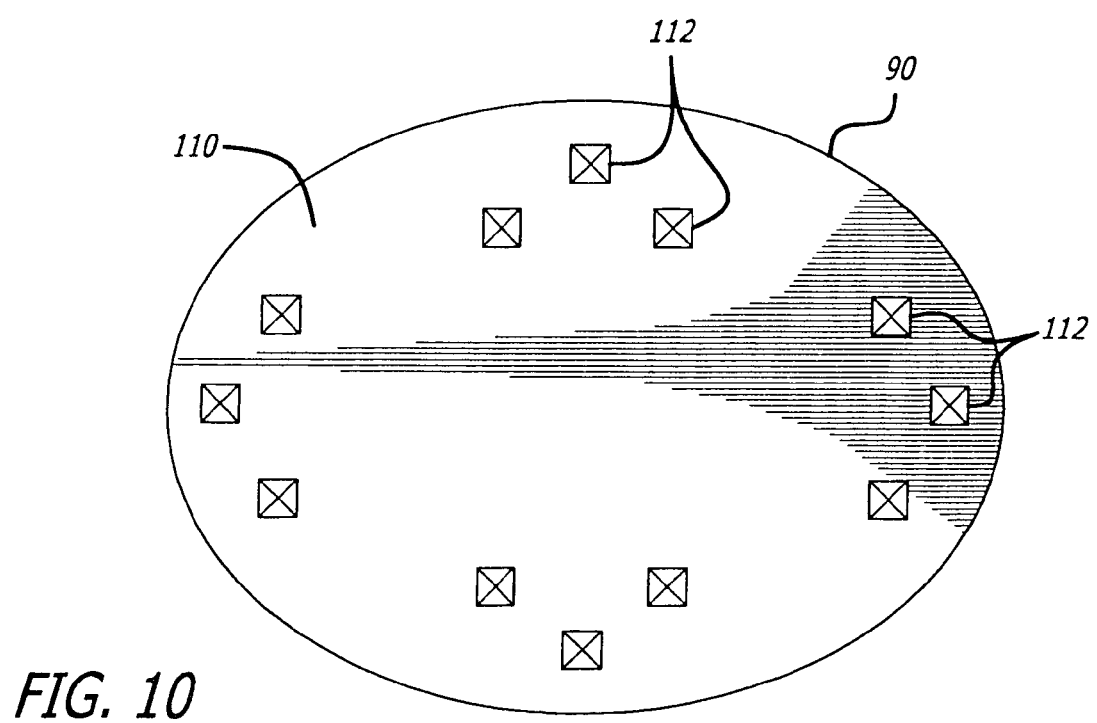
FIG. 10 is a plan view of the FIG. 9 embodiment of the prosthetic spinal disc of the present invention.
Figure 11:
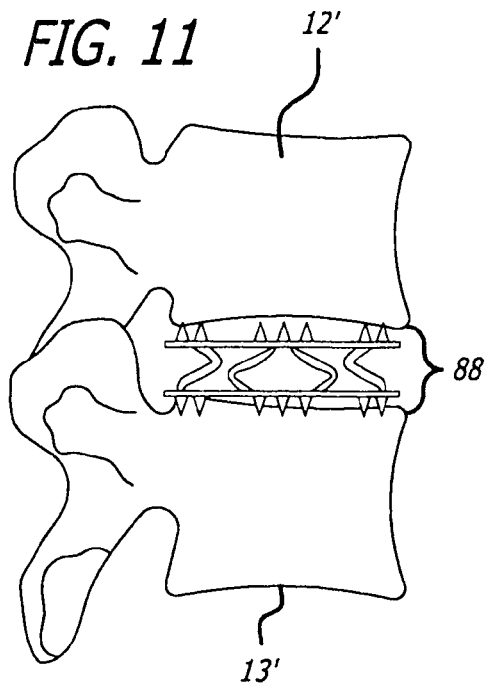
FIGS. 11 and 12 are side sectional views two adjacent vertebrae with one embodiment of the prosthetic spinal disc of the present invention between the vertebrae.

Top surface 110 of upper plate 90 is in contact with the prepared, flat surface of a vertebra (not shown in FIG. 9 but see FIGS. 10 and 11). The top surface 110 is machined to form spikes 112 for engaging and gripping the bone. FIGS. 9 and 10 has 12 spikes in four groups of three. The groups are in triangular arrays. Other arrangements for the spikes are possible. For example, the spikes may be evenly spaced about the periphery of the plate. They may be in straight-line arrays or they may have different spacing. The spikes also can be weld-formed or formed by electric discharge. The spikes in FIGS. 9 and 10 are four-side pyramids. Spikes with three sides or conical or other shapes can be used.

Bottom plate 92 is similar to upper plate 90. Spikes 114 on the bottom plate extend downward from the bottom surface.

The plates 90 and 92 whether flat or curved an be non-parallel with angles between 6° and 12° to accommodate natural disc spacing shapes, e.g., in the lumbar regions. Spring coils of different lateral thicknesses with appropriate spring constants would facilitate the non-parallel plate requirements.

The surgeon also can use adhesive or a porous ingrowth surface coating on the plates and the spikes to secure the section to the vertebral bodies. Doi, U.S. Pat. No. 5,541,184 (1996), is one of many patents showing the use of porous ingrowth the coating for prostheses (a hip prosthesis).

Figure 12:
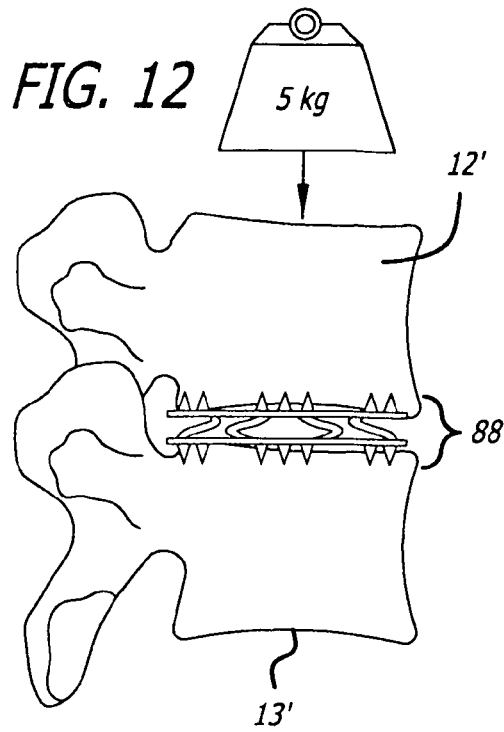

FIGS. 11 and 12 are similar to FIGS. 5 and 6 except that the fitting (i.e., fitting 88 of the exemplary embodiment of FIGS. 9 and 10) replaces the natural disc 14 of FIGS. 5 and 6. Note that when vertebrae 12' and 13' are under load, the springs of the fitting compress. The spinal ligaments and muscles do provide a load to the springs even when the spine is not loaded such as when a person is lying down. Thus, the adjacent vertebrae normally work to compress the prosthesis and its internal springs.

The present invention provides six degrees of freedom. With reference to FIGS. 9 and 10, the present invention allows compression, the movement of plate 90 and 92 toward each other. The present invention likewise permits lateral shear, left/right movement and sagittal shear, forward/back movement in FIG. 10. Likewise, it allows flexion/extension, the movement of the plates away from each other, and lateral bending, movement of a portion of an edge of one plate toward or away from the corresponding portion of the edge of the other plate. Finally, it allows torsion, the rotation of one plate relative to the other plate.

Figure 13:
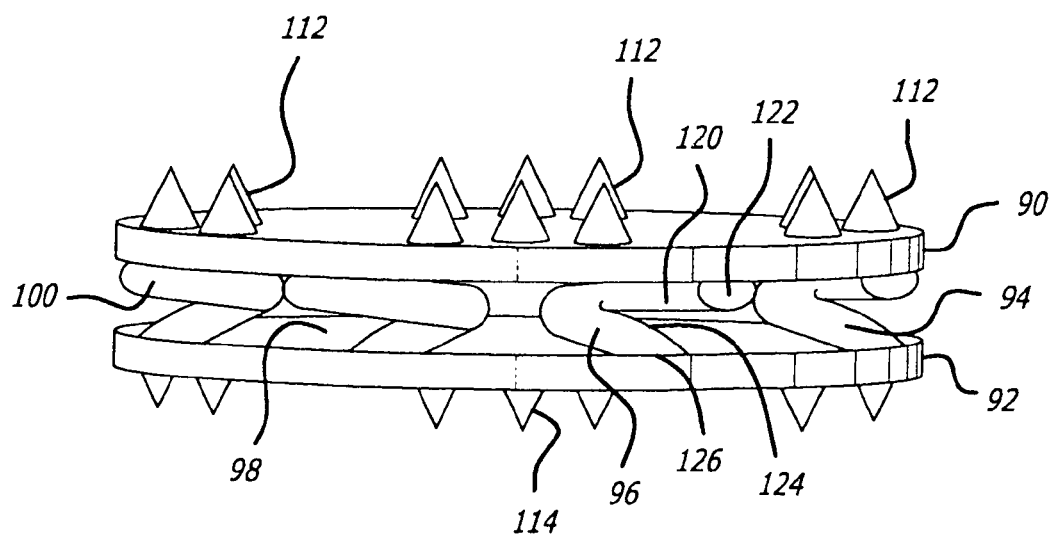
FIG. 13 is another perspective view of one embodiment of the prosthetic spinal disc of the present invention.

FIG. 13, which is similar to FIG. 9, shows how the springs connect to the top and bottom plates 90 and 92. Each spring, e.g., spring 96, is slightly less than a full coil in that embodiment. The spring wire forming spring 96 is cylindrical throughout most of its length. However, at its upper end 120, the portion that faces up is flattened at 122. The flattened surface provides a greater contact area with the inner surface of plate 90. The downward facing opposite end 124 of spring 96 also is flat at 126 for improved contact with bottom plate 92. Ends 120 and 124 are welded to the respective plates. Having a flat surface is not necessary. Welding can secure the springs to the plates even that the spring wire is cylindrical at the connection to the plate. Applicant believes, however, that welding combined with the flat surface yields a better connection. Precision welding of implantable materials such as CoCr, with shapes and dimensions associated with the proposed springs include laser (with inert gas environment) and electron-beam (vacuum) welding techniques.

Figure 14:
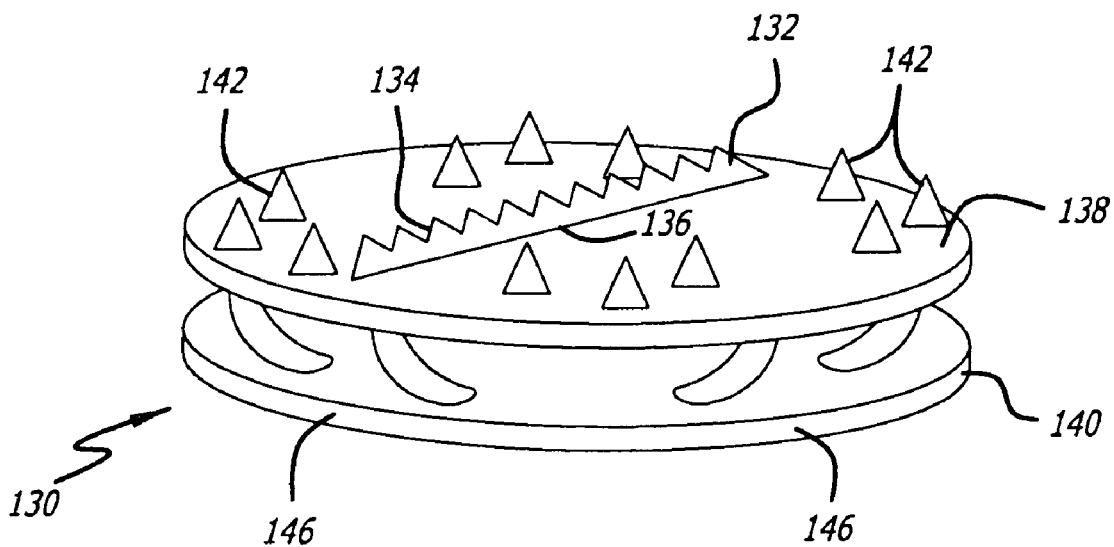
FIG. 14 is a different perspective view of one embodiment of the prosthetic spinal disc of the present invention.

Fitting 130 (FIG. 14) is similar to the previously discussed fittings. However, fitting 130 has an optional keel 132 mounted to the top surface of plate 138. Of course, other embodiments also could benefit from the keel. In addition, the bottom plate 140 may have a downwardly-facing keel (not visible in the drawings). The keels cooperate with spikes 142 and 146 to secure and stabilize the plates 138 and 140 to adjacent vertebrae and prevents the plates from twisting relative to the vertebrae. Note that keel 132 mounts at a 45° angle to the major and minor axes of the plate. The keel that extends from the bottom plate 140 also mounts at an angle to the major and minor axes of that plate and at an angle to keel 132 on the top plate 138. Two keels perpendicular to each other on one or both plates would enhance symmetric loading.

The keel is preferably metal (cobalt-chrome) with a flat bottom surface 136 (or other shape to accommodate the surface of plate 138). The keel is welded to the plate or shape-ground (like spikes) as part of the plate. The top 134 of the keel is serrated to attach to the vertebral bony structure. The keel (and spikes 142 and the top surface of plate 138) may have a covering of porous ingrowth surface coating for improved attachment to the bone.

The previous exemplary embodiments used six springs. Each spring had one full coil or slightly less than a full coil. Eight springs also could be used depending on the size of the plates and the spring coil diameter. A single spring can replace the multiple springs as discussed below, but multiple springs spaced around the periphery of the plates as shown in the exemplary embodiment provide excellent stability for the plates relative to each other. For example, compressive force that would be applied to the edge of adjacent vertebrae would compress the spring or springs in that region. Other springs may not compress or tension, depending on the force.

Figure 15:
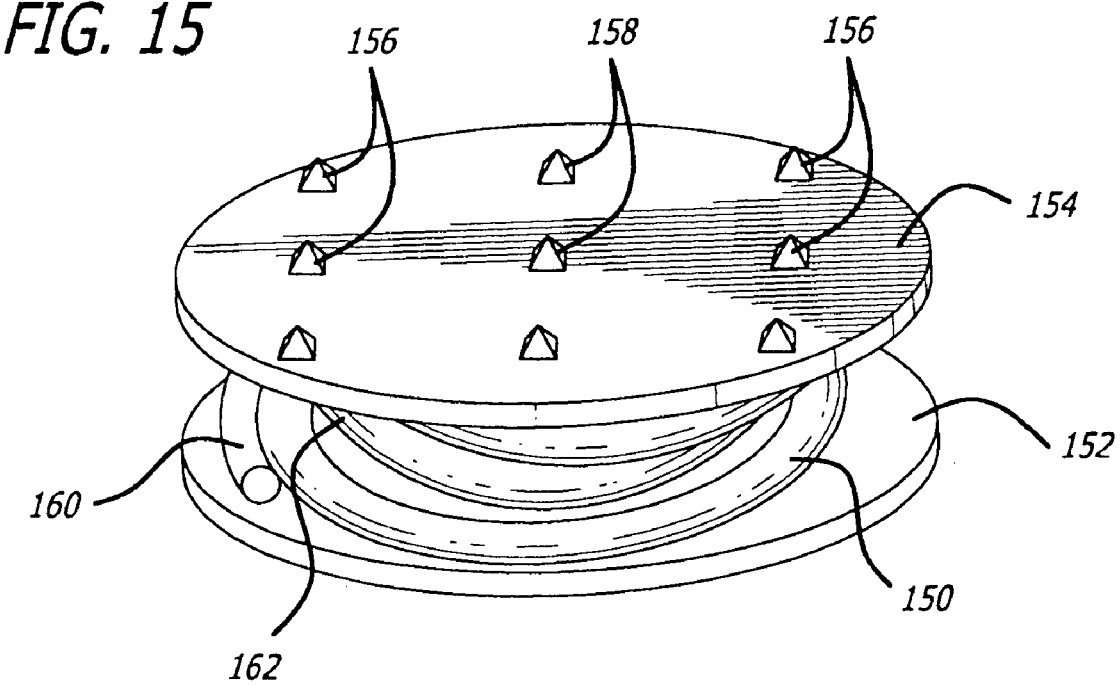
FIG. 15 is a perspective view of another embodiment of the prosthetic spinal disc of the present invention.

The FIG. 15 exemplary embodiment has a single spring 150 mounted between two flat plates 152 and 154. Each plate has a 3×3 array of nine spikes 156 and 158. Spikes 156 and 158 are different shapes, and the shapes and pattern may be interchanged.

Welding the spring to the plates can create a sharp crevice. The body can react to the crevices by depositing tissue that eventually can affect the prosthesis's operation adversely. The present invention uses additional welding material 160 to create a smoother transition between the spring and the plate. The tight dimensions make welding the inside surface 162 of the wire difficult. Instead of using additional welding material to prevent crevices, the spring wire can be modified to yield a smoother transition as discussed with reference to FIG. 14 embodiment.

The inside-facing surface of the plates (e.g., plates 138 and 140 of FIG. 14 or plates 152 and 154 of FIG. 15) may have a groove or a through-hole open slot. The width of the groove or open slot would be approximately equal to the diameter of the spring wire and shaped to receive the end of the spring wire. The portion of the spring wire in the groove is welded in place to secure the spring and to prevent having a crevice.

The exemplary embodiments of FIGS. 18 through 21 share common concepts. Each has top and bottom plates 220 and 222 with one or more internal coil springs. Top surface 224 of plate 220 is in contact with a prepared, flat surface of a vertebra (not shown in FIGS. 18 through 21). The top surface is machined to form new spikes 226 in a 3×3 array for engaging and gripping the bone. The present invention can have a different number, pattern and shape of the spikes. Spikes 230 are also visible on the bottom surface 228 of bottom plate 222. The spikes also can be weld-formed or formed by electric discharge.

Figure 18:
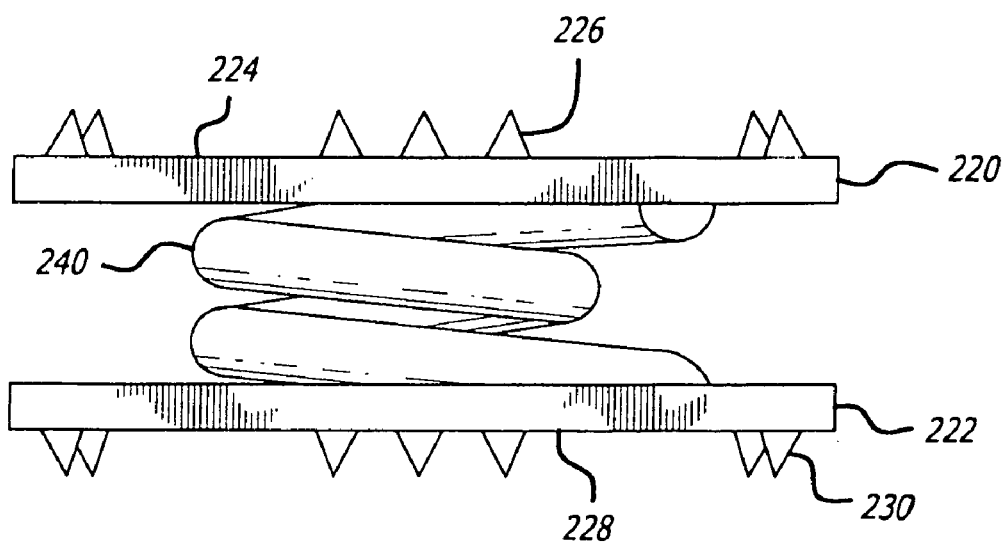
FIG. 18 is a front view of an exemplary embodiment of the prosthetic spinal disc of the present invention.
Figure 19:
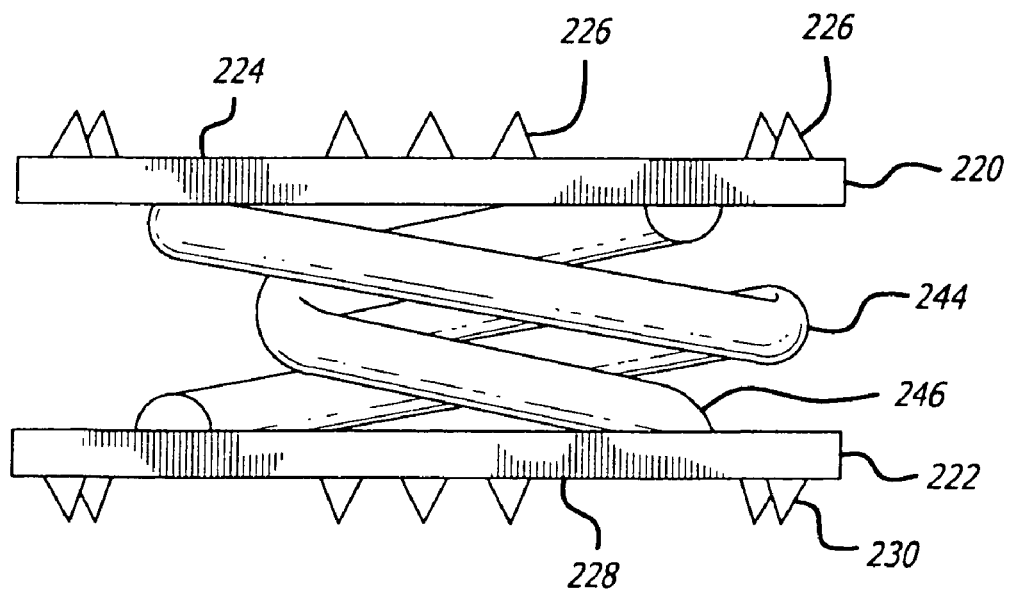
FIG. 19 is a front view of another exemplary embodiment of the prosthetic spinal disc of the present invention.

The exemplary embodiment of FIG. 18 has a single spring 240. The spring has an hourglass shape of approximately two coils. The exemplary embodiment of FIG. 19 has two interweaved springs 244 and 246 that are offset approximately 180° from each other. Each spring is approximately one coil.

Applicant contemplates that the spring wire for springs 244 and 246 (FIG. 19) will have a 0.00127 in (0.0323 mm) radius. The two-spring arrangement provides increased stiffness over a single spring coil. The present invention can obtain greater stiffness with similar springs having a 0.001625 in (0.04128 mm) radius. See springs 252 and 254 in FIG. 21. At least in theory, the surgeon could use stiffer or more yielding springs for persons of different size or weight or for different vertebrae. On the other hand, stiffer springs (i.e., larger diameter spring wire) may prove better for all patients.

While exemplary embodiments show a single spring, applicant believes that multiple springs are better especially in sets of two springs having the opposite windings. Therefore, as the springs compress, they tend to cancel torque the each generates. Applicant also believes that six or eight springs spaced about the periphery not only cancel torque but enhance movement and force absorption while allowing six degrees of freedom.

The springs can be wound in coarse spirals. For spring 260 (FIGS. 20A-20C), The spring wire begins in the top center 262 and spirals outward to outside loop 264. It then loops downward at 266 to outer loop 268 and into inner loop 270. The spring can be used between two plates similar to the embodiments of FIGS. 18 through 21. Alternatively, regions of the top- and bottom-facing surfaces of the spring could have spikes 272 machined into the spring wire for engaging the bone directly. In addition, the inner loops 262 and 270 may be higher than the outer loops 264 and 268 such that the upper portion of the spring is convex. Instead of preparing the vertebral bone in a flat plane, the surgeon could prepare it with a concave shape to mate with the convex portion of such a spring. Likewise, applicants could adapt the plates of the prosthesis into a convex shape.

A spring such as spring 260 (FIG. 20A-20C), whether it has spikes for attaching to bone or no spikes for attaching to plates, can provide non-linear force to displacement. The stiffness of a spring, k, is defined by the following formula:

$$k = \frac{d^4 G}{8D^3 N} \quad (1)$$

where d is the wire diameter;
G is the shear modulus of the material;
D is the spring diameter; and
N is the number of coils.

Thus, varying the wire diameter and the coil diameter changes the spring stiffness (all other things being equal). When the coils or wire diameter are not constant, the spring stiffness is not linear. Therefore, the displacement is not a linear function of the applied force.

Figure 20A:
FIGS. 20A, 20B and 20C are respectively top, side and perspective views of a spring used in exemplary embodiments of the present invention. A computer program used some designs for analysis of forces at different positions along the spring wire. Insofar as the spring wire appears to have rings, the computer program used the sections between the rings for analysis.
Figure 20B:
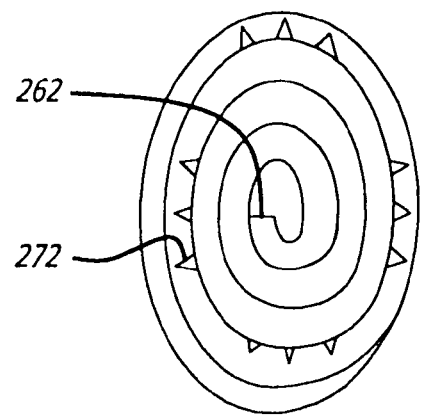
Figure 20C:
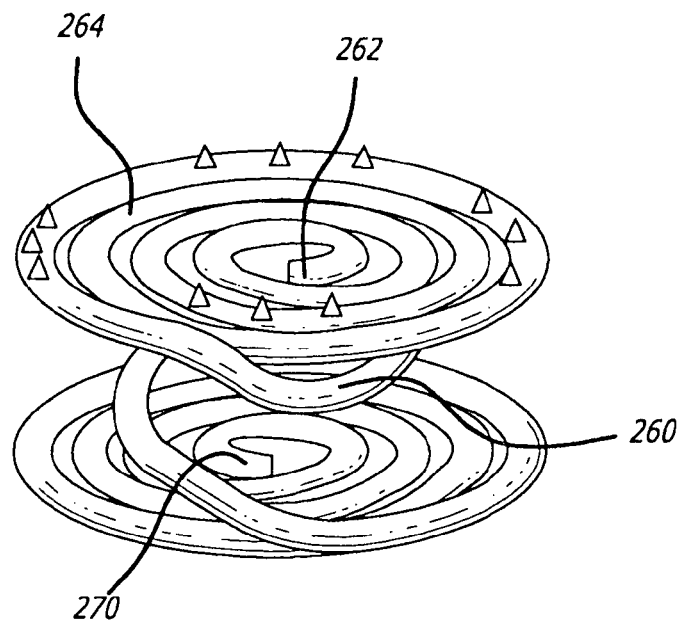
Figure 21:
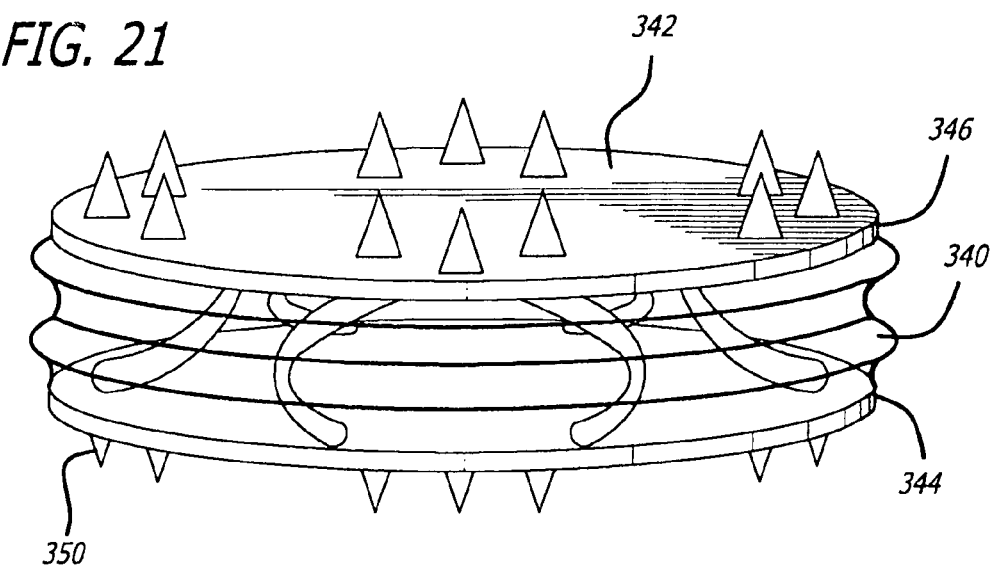
FIG. 21 is a perspective view of an embodiment of the present invention that has a skirt or bellows welded to the outside of the prosthesis.

Referring to FIG. 20A-20C, the diameter of outer loops 264 and 268 are greater than the diameter of inner loops 262 and 270. Because the stiffness is inversely related to the coil diameter, the outer loop has less stiffness than the inner loop. Therefore, varying the applied load to the spring will yield a non-linear displacement.

Formula (1) also shows that spring stiffness is directly related to wire diameter. Thus, one could have non-linear response from the spring by having a non-constant wire diameter. For example, a length of the spring wire near the end of the spring of could taper to a larger or smaller diameter than other sections of the spring. The taper also could be at the center. Alternatively, several sections of the wire could have a decreased or increased diameter section. Thus, in FIG. 16, as an example, the spring wire of outer coil 84a is diameter $d_1$, the diameter of center coil's 84b is $d_2$, and the diameter of inner coil 84c diameter is $d_3$. Diameter $d_1$ could be greater than or less than diameter $d_2$, which could be greater than or less than diameter $d_3$.

Having non-circular sections as discussed above also would yield a non-linear response.

Allowing contact between some adjacent coils is another way to provide non-linear response subject to the caveat against allowing such contact. The spring compresses at one rate $k_1$ until the two (or more) coils touch each other and at another rate $k_2$ after the coils contact each other.

Figure 24:
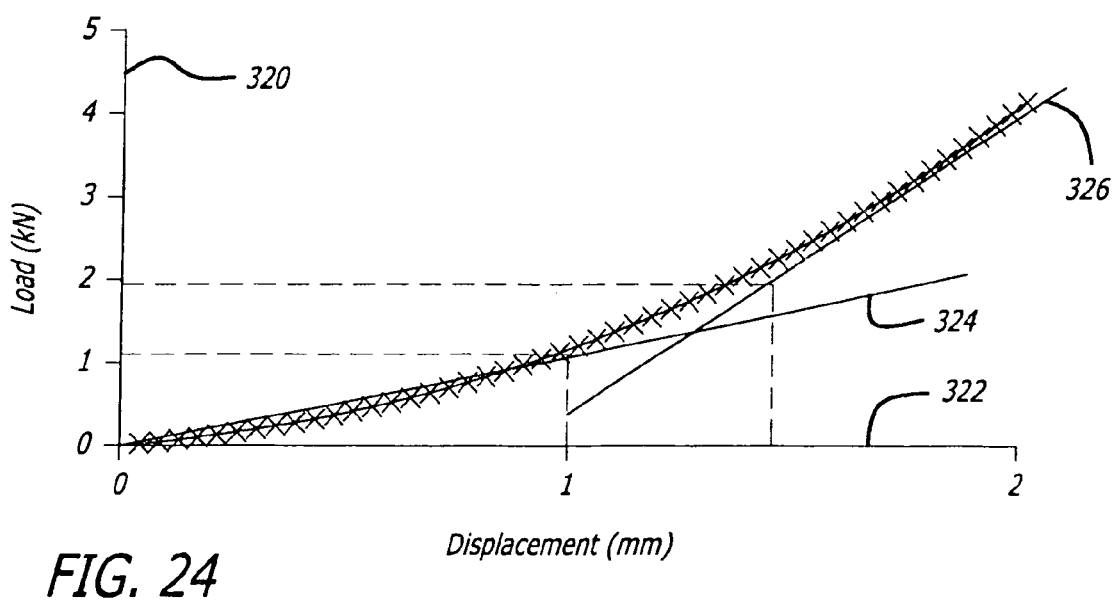
FIG. 24 is a graph of vertical displacement of one plate of the prosthesis relative to the other plate as a function of load on the prosthesis.

Having non-linear response and the resulting variation in the load/displacement characteristics can be beneficial. FIG. 24 shows a graph of one possible load/displacement curve.

The vertical axis 320 shows the load (in kN), and the horizontal axis 322 show the displacement (in mm). Through a load of about 1 kN, displacement rises along slope 324 to 1 mm, but for higher loads above 1 kN, slope 326 becomes more vertical. Thus, at a 2 kN load, the displacement is about 1.5 mm. By having a lower slope at lower loads, the disc can be relatively flexible. Having a higher slope at higher loads can prevent the disc from bottoming out, i.e., all adjacent coils contacting each other or contacting the plates such that the springs would absorb no further load.

Applicant anticipates that in embodiments such as FIG. 9 with multiple springs, all the springs would have similar characteristics, but that is not necessarily required.

The Bryan cervical disc (FIG. 8) has a flexible membrane extending around its periphery. Applicant contemplate using an optional flexible membrane attached to the edge of the top and bottom plates in the exemplary embodiment of the present invention.

Figure 22:
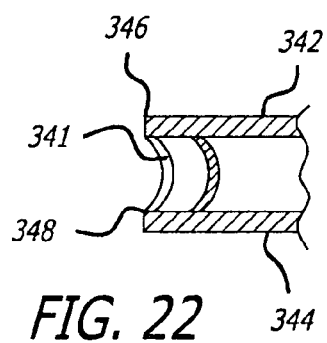
FIG. 22 and FIG. 23 are sectional views showing connections of the bellows to the plates.
Figure 23:
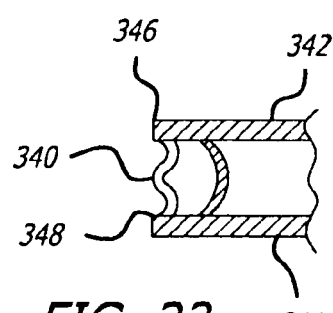

Applicant is concerned that such a membrane, which appears to be a plastic or rubber, would deteriorate and allow its breach. An open membrane (or no membrane) would allow fibrous growth on the inside of the disc. In addition, loose debris would not be contained Therefore, the present invention uses a CoCr foil to act as a barrier. In an exemplary embodiment, the foil (FIG. 21-23) is in the form of bellows 340 having one or more corrugations (compare bellows 340 in FIG. 23 with bellows 341 in FIG. 22). A corrugation is a half-circle. The corrugated bellows design permits combined six degrees of motion. The bellows is fabricated as a foil cylinder. The top and bottom edges are welded to peripheral edge 346 of plate 342 and to peripheral edge 348 of plate 344. Welding of the bellows encloses and seal the gap 350 between the plates. Having the bellow's ends (single, half-circle or multiple) tangent to the plate surface is preferred. That arrangement permits continuous or spot welding. The bellows are sufficiently spaced from the springs 352 (FIGS. 21-23) to remain out of contact with each other.

Welding likely is the best attachment, but rings seating in grooves around the plates could secure the bellows to the plates. Similarly, adhesive or other mechanical attachments may be adequate.

Though the specification describes particular embodiments of the present invention, those of ordinary skill can devise variations of the present invention without departing from the inventive concept.

I claim:

1. A prosthesis for being received between two adjacent vertebrae in a body comprising:
   a) a spring formed of spring wire having two ends;
   b) at least one end coil at each end of the spring wire being wound into a configuration that meshes with the adjacent vertebrae; and
   c) spikes extending outward from the at least one end coil for directly connecting to the adjacent vertebrae.

2. The prosthesis of claim 1 wherein the spring is a coil spring, at least a portion of the coil of the spring having a non-circular cross-section.

3. The prosthesis of claim 1 wherein the spring is a coil spring.

4. The prosthesis of claim 1 wherein the spring is formed of spring wire that has more than one outer dimensions over portions of the spring wire.

5. The prosthesis of claim 1 wherein the spring is a coil spring, the spring further including means to prevent adjacent coils of the coil spring from contacting each other when the spring is compressed to its maximum compression in the body.

6. The prosthesis of claim 5 wherein the means to prevent adjacent coils from contacting each other comprises the provision of adjacent coils having different effective diameters.

7. The prosthesis of claim 5 wherein the means to prevent adjacent coils from contacting each other comprises the provision of the spring having an hourglass shape.

8. The prosthesis of claim 5 wherein the means to prevent adjacent coils from contacting each other comprises the provision of the spring having a top and bottom and a center between the top and bottom, the diameter of the spring at its top and bottom being greater than the diameter at its center.

9. The prosthesis of claim 1 wherein at least a portion of the spring wire in the conforming portion is flat, the spikes extending from the flat portion of spring wire.

10. A prosthesis for being received between adjacent upper and lower vertebrae in a body, the upper vertebra having a surface facing downward, and the lower vertebra having a surface facing upward, the prosthesis comprising:
    a) a coil spring formed of spring wire having first and second ends, the first end being adjacent the upper vertebra, and the second end being adjacent the lower vertebra;
    b) a conforming portion of the spring adjacent at least the first end, the spring wire in the conforming portion being wound into multiple coils that generally conform to and directly contact the surface of the upper vertebra; and
    c) wherein the multiple coils of the conforming portion have outer helixes and inner helixes, the spring wire in at least one of the outer helixes having a different diameter that the spring wire of at least one of the inner helixes.

11. A prosthesis for being received between adjacent upper and lower vertebrae in a body, the upper vertebra having a surface facing downward, and the lower vertebra having a surface facing upward, the prosthesis comprising:
    a) a coil spring formed of spring wire having first and second ends, the first end being adjacent the upper vertebra, and the second end being adjacent the lower vertebra;
    b) a conforming portion of the spring adjacent at least the first end, the spring wire in the conforming portion being wound into multiple coils that generally conform to and directly contact the surface of the upper vertebra; and
    c) wherein the multiple coils of the conforming portion have outer helixes and inner helixes, the spring wire in at least one of the outer helixes having a different stiffness that the spring wire of at least one of the inner helixes.

12. A prosthesis for being received between adjacent upper and lower vertebrae in a body, the upper vertebra having a surface facing downward, and the lower vertebra having a surface facing upward, the prosthesis comprising:
    a) a coil spring formed of spring wire having first and second ends, the first end being adjacent the upper vertebra, and the second end being adjacent the lower vertebra;
    b) a conforming portion of the spring adjacent at least the first end, the spring wire in the conforming portion being wound into multiple coils that generally conform to and directly contact the surface of the upper vertebra; and c) wherein the spring is a coil spring, the spring further including means to prevent adjacent coils of the coil spring from contacting each other when the spring is compressed to its maximum compression in the body.

13. The prosthesis of claim 12 wherein the means to prevent adjacent coils from contacting each other comprises the provision of adjacent coils having different effective diameters.

14. The prosthesis of claim 12 wherein the means to prevent adjacent coils from contacting each other comprises the provision of the spring having an hourglass shape.

15. The prosthesis of claim 12 wherein the means to prevent adjacent coils from contacting each other comprises the provision of the spring having a center between the first and second ends, the diameter of the spring adjacent to the first and second ends being greater than the diameter of the spring between the first and second ends.

16. A prosthesis for being received between adjacent upper and lower vertebrae in a body, the upper vertebra having a surface facing downward, and the lower vertebra having a surface facing upward, the prosthesis comprising:
   a) a coil spring formed of spring wire having first and second ends, the first end being adjacent the upper vertebra, and the second end being adjacent the lower vertebra;
   b) a conforming portion of the spring adjacent at least the first end, the spring wire in the conforming portion being wound into multiple coils that generally conform to and directly contact the surface of the upper vertebra; and
   c) further compressing a plurality of spikes extending from the conforming portion toward the surface of the vertebrae.

17. A prosthesis for being received between adjacent upper and lower vertebrae in a body, the upper vertebra having a surface facing downward, and the lower vertebra having a surface facing unward, the prosthesis comprising:
   a) a coil spring formed of spring wire having first and second ends, the first end being adjacent the upper vertebra, and the second end being adjacent the lower vertebra;
   b) a conforming portion of the spring adjacent at least the first end, the spring wire in the conforming portion being wound into multiple coils that generally conform to and directly contact the surface of the upper vertebra; and
   c) wherein at least a portion of the spring wire at the conforming portion is flat, the prosthesis further comprising a plurality of spikes extending from the flat portion of the conforming portion toward the surface of the upper vertebra.

* * * * *

UNITED STATES PATENT AND TRADEMARK OFFICE
CERTIFICATE OF CORRECTION

| | |
|---|---|
| PATENT NO. | : 7,309,357 B2 |
| APPLICATION NO. | : 11/027728 |
| DATED | : December 18, 2007 |
| INVENTOR(S) | : Kim |

Page 1 of 1

It is certified that error appears in the above-identified patent and that said Letters Patent is hereby corrected as shown below:

Column 16 line 10, replace "unward" with --upward--

Signed and Sealed this

Sixth Day of May, 2008

JON W. DUDAS
*Director of the United States Patent and Trademark Office*